US012642961B2

(12) United States Patent
Karunasiri et al.

(10) Patent No.: US 12,642,961 B2
(45) Date of Patent: Jun. 2, 2026

(54) SYSTEMS AND METHODS FOR DETERMINING EFFECTS OF A TRIGGERING EVENT THAT OCCURS DURING USE OF A HEARING DEVICE

(71) Applicant: Advanced Bionics AG, Staefa (CH)

(72) Inventors: R. Tissa Karunasiri, Valencia, CA (US); Anthony J. Spahr, Newhall, CA (US); Scott Kenneth Arfin, Valencia, CA (US); Phillipp Hehrmann, Hannover (DE)

(73) Assignee: Advanced Bionics AG, Staefa (CH)

( * ) Notice: Subject to any disclaimer, the term of this patent is extended or adjusted under 35 U.S.C. 154(b) by 636 days.

(21) Appl. No.: 18/024,863

(22) PCT Filed: Oct. 30, 2020

(86) PCT No.: PCT/US2020/058314
§ 371 (c)(1),
(2) Date: Mar. 6, 2023

(87) PCT Pub. No.: WO2022/093272
PCT Pub. Date: May 5, 2022

(65) Prior Publication Data
US 2024/0285939 A1 Aug. 29, 2024

(51) Int. Cl.
A61N 1/36 (2006.01)
A61N 1/05 (2006.01)
(Continued)

(52) U.S. Cl.
CPC ............. *A61N 1/08* (2013.01); *A61N 1/0541* (2013.01); *A61N 1/36038* (2017.08);
(Continued)

(58) Field of Classification Search
CPC ........................ A61N 1/36036; A61N 1/36038
See application file for complete search history.

(56) References Cited

U.S. PATENT DOCUMENTS 8,498,706 B2 7/2013 Pei et al.
8,634,918 B2 1/2014 Chambers
(Continued)

FOREIGN PATENT DOCUMENTS

NO 2012160527 11/2012
WO 2013142844 9/2013
(Continued)

OTHER PUBLICATIONS

"International Search Report and Written Opinion mailed Aug. 3, 2021 in corresponding International Application No. PCT/US2020/058314 with the International Filing Date of Oct. 30, 2020".

*Primary Examiner* — George R Evanisko
(74) *Attorney, Agent, or Firm* — ALG Intellectual Property, LLC

(57) ABSTRACT

An exemplary system includes a sensor configured to output sensor data and a hearing device comprising a processor. The processor of the hearing device may be configured to detect, based on the sensor data, a triggering event that occurs during use of the hearing device by a recipient of the hearing device. The triggering event may be indicative of possible damage to at least one of the hearing device or the recipient. The processor may further, apply, in response to the detecting of the triggering event, stimulation to the recipient, detect a signal that occurs in response to the stimulation and that is recorded by an electrode associated with the hearing device, compare the signal to a baseline signal recorded by the electrode prior to the triggering event, and determine, based on the comparing of the signal to the baseline signal, an operational effectiveness state of the hearing device.

20 Claims, 9 Drawing Sheets

(51) Int. Cl.

| | |
|---|---|
| *A61N 1/08* | (2006.01) |
| *A61N 1/372* | (2006.01) |

(52) U.S. Cl.

CPC ..... *A61N 1/36139* (2013.01); *A61N 1/36142* (2013.01); *A61N 1/36167* (2013.01); *A61N 1/36185* (2013.01); *A61N 1/37217* (2013.01); *A61N 1/37247* (2013.01); *A61N 2001/083* (2013.01)

(56) References Cited

U.S. PATENT DOCUMENTS

| | | | |
|---|---|---|---|
| 9,265,431 B2 | 2/2016 | Hincapie Ordonez et al. | |
| 10,272,010 B2 | 4/2019 | Freeman et al. | |
| 2009/0112292 A1 | 4/2009 | Armstrong | |
| 2009/0299421 A1 | 12/2009 | Sawchuk | |
| 2009/0312810 A1 | 12/2009 | Yonce et al. | |
| 2011/0066206 A1 | 3/2011 | Kuhn et al. | |
| 2011/0288603 A1 | 11/2011 | Kim et al. | |
| 2012/0046711 A1 | 2/2012 | Osorio | |
| 2017/0360364 A1 | 12/2017 | Heasman | |
| 2018/0056058 A1 | 3/2018 | Heasman | |
| 2020/0054877 A1* | 2/2020 | Calixto | A61N 1/36132 |
| 2020/0330763 A1 | 10/2020 | Hamacher | |

FOREIGN PATENT DOCUMENTS

| | | |
|---|---|---|
| WO | 2014089476 | 6/2014 |
| WO | 2016057017 | 4/2016 |
| WO | 2020053725 | 3/2020 |
| WO | 2020139397 | 7/2020 |

* cited by examiner

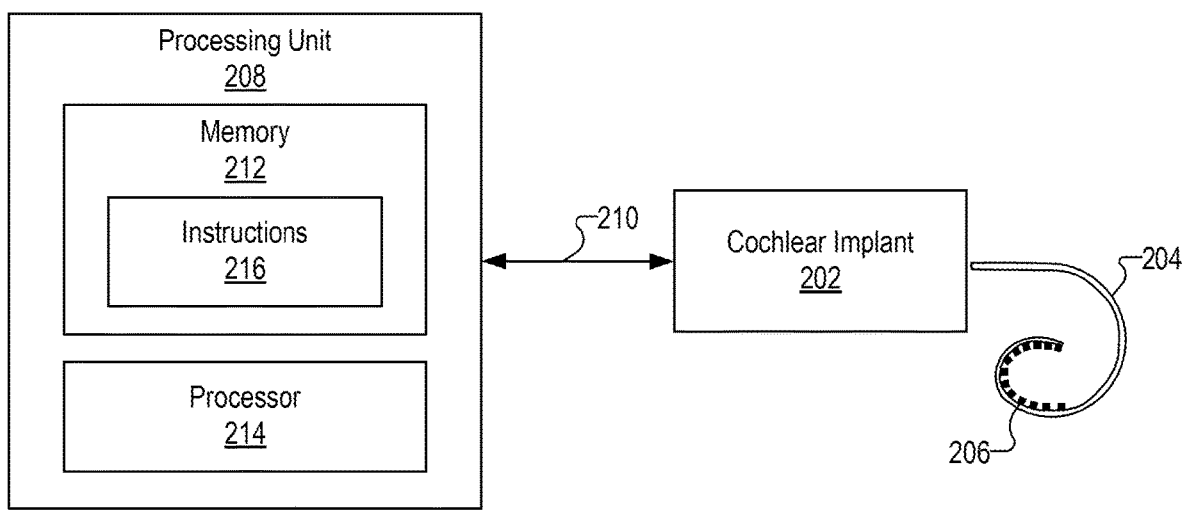
Fig. 2

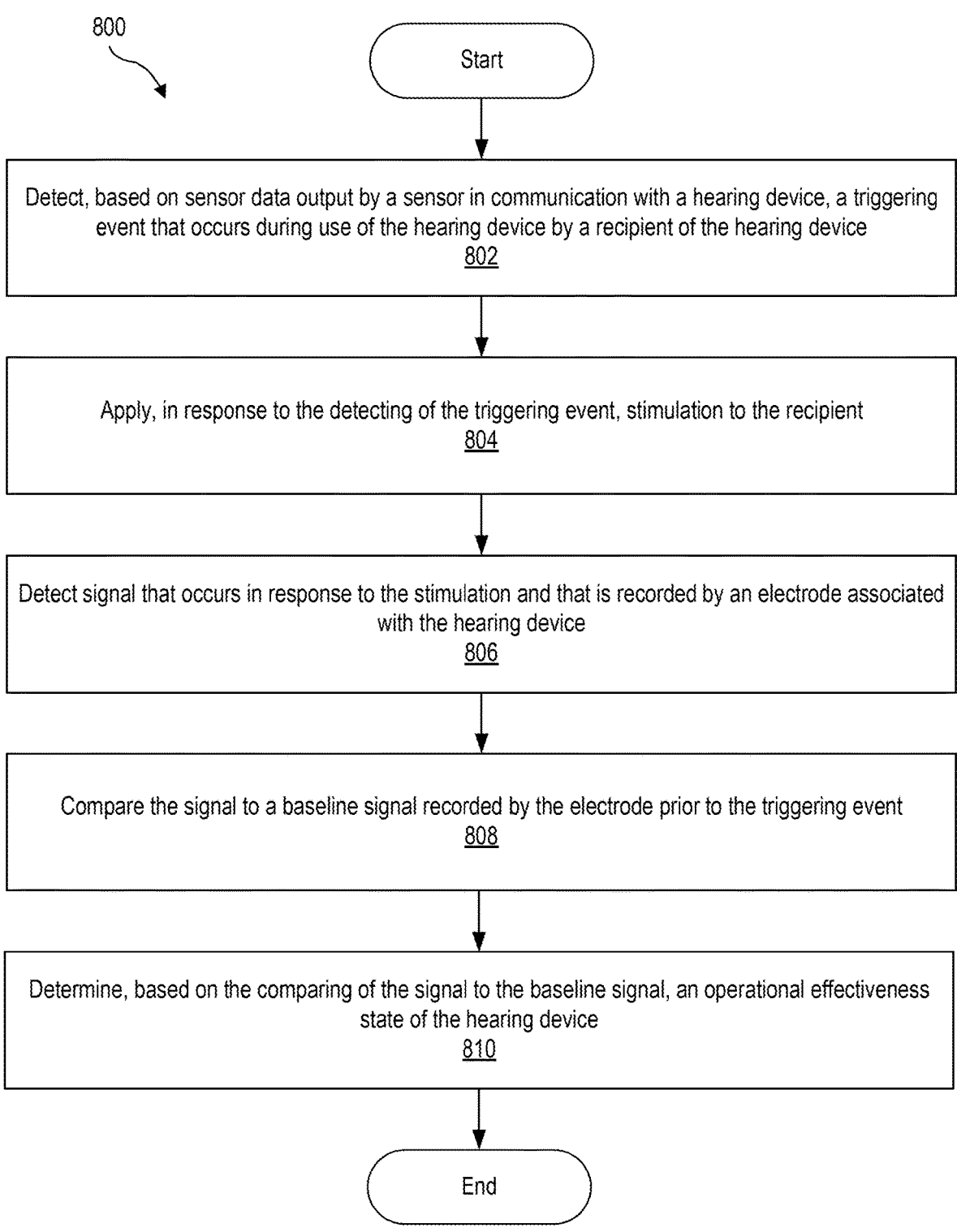

800

Start

Detect, based on sensor data output by a sensor in communication with a hearing device, a triggering event that occurs during use of the hearing device by a recipient of the hearing device
802

Apply, in response to the detecting of the triggering event, stimulation to the recipient
804

Detect signal that occurs in response to the stimulation and that is recorded by an electrode associated with the hearing device
806

Compare the signal to a baseline signal recorded by the electrode prior to the triggering event
808

Determine, based on the comparing of the signal to the baseline signal, an operational effectiveness state of the hearing device
810

End

Fig. 8

SYSTEMS AND METHODS FOR DETERMINING EFFECTS OF A TRIGGERING EVENT THAT OCCURS DURING USE OF A HEARING DEVICE

BACKGROUND INFORMATION

Hearing devices such as those used in cochlear implant systems are used to provide, restore, and/or improve the sense of hearing to recipients with severe or profound hearing loss. Conventional cochlear implant systems include various components configured to be implanted within a recipient (e.g., a cochlear implant, implant circuitry, an antenna, and an electrode lead) and various components configured to be located external to the recipient (e.g., a sound processor, a battery, and a microphone).

During use of a hearing device, an event may occur that may cause damage to the hearing device and/or a recipient of the hearing device. For example, a mechanical impact to the head of a recipient of a cochlear implant system may cause damage to implant circuitry, a housing of the cochlear implant, and/or either temporarily or permanently affect an electrode-nerve interface of the electrode lead of the cochlear implant. This may result in decreased performance of the cochlear implant system, further loss in hearing capacity of the recipient, and/or bodily harm to the recipient. Moreover, such an event may result in the recipient of a hearing device experiencing increased anxiety and apprehension because the recipient may not know whether damage occurred as a result of the event and/or what needs to be done to address it.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 2 shows an exemplary cochlear implant system.

FIG. 8 illustrates an exemplary method according to principles described herein.

DETAILED DESCRIPTION

Figure 1:
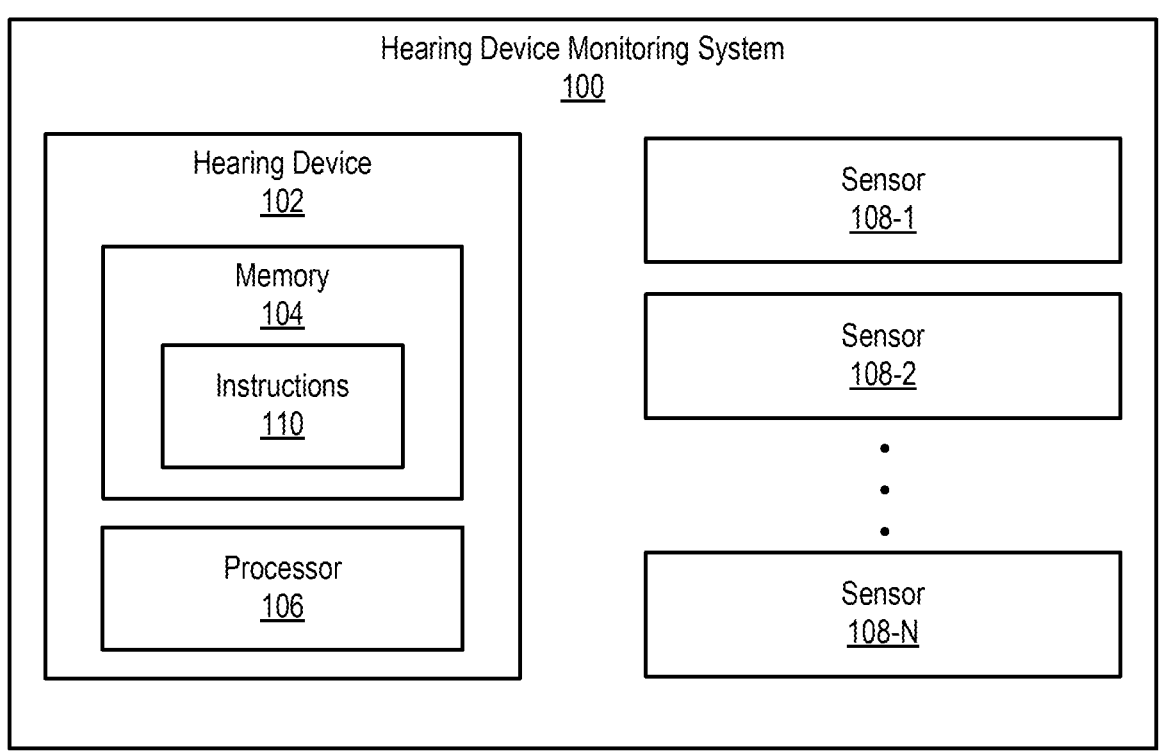
FIG. 1 shows an exemplary hearing device monitoring system that may be implemented according to principles described herein.

Systems and methods for determining effects of a triggering event that occurs during use of a hearing device are described herein. For example, a system may include a sensor configured to output sensor data and a hearing device comprising a processor. The processor of the hearing device may be configured to detect, based on the sensor data, a triggering event that occurs during use of the hearing device by a recipient of the hearing device. The triggering event may be indicative of possible damage to at least one of the hearing device or the recipient. The processor may be further configured to apply, in response to the detecting of the triggering event, stimulation to the recipient, detect a signal that occurs in response to the stimulation and that is recorded by an electrode associated with the hearing device, compare the signal to a baseline signal recorded by the electrode prior to the triggering event, and determine, based on the comparing of the signal to the baseline signal, an operational effectiveness state of the hearing device.

As used herein, a "triggering event" may include any event or combination of events that may occur during use of a hearing device and that may negatively affect operation of the hearing device and/or may be indicative of possible damage to the hearing device and/or the recipient. For example, a triggering event may include a mechanical force impact (e.g., due to a fall, an impact the head of a recipient, etc.), an electrostatic discharge (e.g., in a cochlear implant), an error in telemetry data, an acoustic event (e.g., a sudden loud noise), a medical condition (e.g., tissue inflammation), and/or any other suitable event or combination of events. Specific examples of triggering events are described herein.

The damage caused by triggering events such as those described herein may include any type of damage that may be caused to a hearing device or a recipient. For example, the damage to the recipient may include physical damage to the body to the recipient, non-physical damage to the recipient (e.g., increased anxiety, poor mental health, etc.), and/or any other type of damage. The damage to the hearing device may include destruction of any component or part of the hearing device, damage to data that that may cause loss of function of the hearing device (e.g., corrupted programming, settings, etc.), and/or any other type of damage.

As used herein, an "operational effectiveness state" of a hearing device may represent any state associated with a hearing device and/or a recipient of the hearing device subsequent to the occurrence of a triggering event. In certain examples, an operational effectiveness state may indicate whether a hearing device is in a fully operational state, a partially operational state, a damaged state, a non-operational state, or any other suitable operational effectiveness state. Additionally or alternatively, an operational effectiveness state may be indicative of damage or lack of damage to the recipient as a result of a triggering event.

To illustrate an example, during use of a hearing device (e.g., a cochlear implant), a recipient of the hearing device may experience an impact to their head because of a fall down a flight of stairs. Subsequent to the fall, the recipient may wonder whether their hearing device and/or their hearing capacity has been damaged or otherwise negatively affected as a result of the impact. In such an example, a system such as described herein may detect, based on sensor data detected by a sensor (e.g., an accelerometer) associated with the hearing device, a triggering event in the form of an impact to the head of the recipient of the hearing device. In response to the detecting of the triggering event, the system may apply stimulation (e.g., by way of an implanted electrode in a cochlear implant) to the recipient. The system may detect a signal (e.g., an evoked response) that occurs in response to the stimulation and that is recorded by an electrode associated with the hearing device. The system may compare the signal to a baseline signal (e.g., a signal indicative of normal operation of the hearing device) recorded by the electrode prior to the triggering event. Based on the comparing of the signal to the baseline signal, the system may determine an operational effectiveness state of the hearing device. For example, if the signal and the baseline signal are within a predefined degree of similarity to each other, the system may determine that the hearing device is in a fully operational state in which the hearing device sustained no damage as a result of the impact to the head of the recipient. Alternatively, if the signal and the baseline signal are not within the predefined degree of similarity, the system may determine that the hearing device is in a damaged state because of the impact.

In certain examples, the system may be configured to notify the recipient in any suitable manner regarding the determined operational effectiveness state of the hearing device. For example, if the hearing device is in a fully operational state in the example described above, the system may be configured to provide a first notification (e.g., a pre-recorded audio message) to the user by way of the hearing device indicating that the hearing device is working properly and/or has sustained no damage as a result of the impact. Alternatively, if the hearing device is in a damaged state in the example described above, the system may provide a second notification (e.g., a pre-recorded audio message) informing the recipient regarding what has been done and/or what needs to be done to address the damage caused by the impact.

By determining an operational effectiveness state of a hearing device, the systems and methods described herein may optimize operation of a hearing device by providing a mechanism whereby effects to the hearing device as a result of a triggering event may be evaluated and addressed in real time during use of the hearing device. In addition, the systems and methods described herein may have high sensitivity, a low false alarm rate, and may result in minimal interruption in user experience. Moreover, the systems and methods described herein may facilitate providing useful information to a recipient regarding an operational effectiveness state, which may result in the recipient experiencing reduced anxiety and/or increased peace of mind subsequent to a triggering event as compared to conventional methods. These and other benefits and advantages of the systems and methods described herein will be made apparent herein.

FIG. 1 illustrates an exemplary hearing device monitoring system 100 that may be configured according to principles described herein. As shown, hearing device monitoring system 100 may include, without limitation, a hearing device 102 including a memory 104 and a processor 106, and sensors 108 (e.g., sensors 108-1 through 108-N) selectively and communicatively coupled to one another.

Hearing device 102 may be implemented by any device configured to provide or enhance hearing to a user. For example, hearing device 102 may be implemented by a hearing aid configured to amplify audio content to a user, a sound processor included in a cochlear implant system configured to apply electrical stimulation representative of audio content to a user, a sound processor included in a stimulation system configured to apply electrical and acoustic stimulation to a user, or any other suitable hearing prosthesis or combination of hearing prostheses. In some examples, hearing device 102 may be implemented by a fully implanted hearing system such as a fully implanted cochlear implant system. In some examples, hearing device 102 may be implemented by a behind-the-ear ("BTE") hearing device configured to be worn behind an ear and/or an in-the-ear ("ITE") hearing device configured to be worn at least partially within an ear canal of a user.

FIG. 2 illustrates an exemplary implementation of hearing device 102 as a cochlear implant system 200 configured to be used by a recipient. As shown, cochlear implant system 200 includes a cochlear implant 202, an electrode lead 204 physically coupled to cochlear implant 202 and having an array of electrodes 206, and a processing unit 208 configured to be communicatively coupled to cochlear implant 202 by way of a communication link 210.

The cochlear implant system 200 shown in FIG. 2 is unilateral (i.e., associated with only one ear of the recipient). Alternatively, a bilateral configuration of cochlear implant system 200 may include separate cochlear implants and electrode leads for each ear of the recipient. In the bilateral configuration, processing unit 208 may be implemented by a single processing unit configured to interface with both cochlear implants or by two separate processing units each configured to interface with a different one of the cochlear implants.

Cochlear implant 202 may be implemented by any suitable type of implantable stimulator configured to apply electrical stimulation to one or more stimulation sites located along an auditory pathway of the recipient. In some examples, cochlear implant 202 may additionally or alternatively apply nonelectrical stimulation (e.g., mechanical and/or optical stimulation) to the auditory pathway of the recipient. In certain examples, cochlear implant system 200 may include or otherwise be associated with a brainstem implant and/or any other type of device that may be implanted within the recipient and configured to apply electrical stimulation to one or more stimulation sites located along an auditory pathway of the recipient.

In some examples, cochlear implant 202 may be configured to generate electrical stimulation representative of an audio signal processed by processing unit 208 in accordance with one or more stimulation parameters transmitted to cochlear implant 202 by processing unit 208. Cochlear implant 202 may be further configured to apply the electrical stimulation to one or more stimulation sites (e.g., one or more intracochlear locations) within the recipient by way of one or more electrodes 206 on electrode lead 204. In some examples, cochlear implant 202 may include a plurality of independent current sources each associated with a channel defined by one or more of electrodes 206. In this manner, different stimulation current levels may be applied to multiple stimulation sites simultaneously by way of multiple electrodes 206.

Cochlear implant 202 may additionally or alternatively be configured to generate, store, and/or transmit data. For example, cochlear implant may use one or more electrodes 206 to record one or more signals (e.g., one or more voltages, impedances, evoked responses within the recipient, and/or other measurements) and transmit, by way of communication link 210, data representative of the one or more signals to processing unit 208. In some examples, this data is referred to as back telemetry data.

Electrode lead 204 may be implemented in any suitable manner. For example, a distal portion of electrode lead 204 may be pre-curved such that electrode lead 204 conforms with the helical shape of the cochlea after being implanted. Electrode lead 204 may alternatively be naturally straight or of any other suitable configuration.

In some examples, electrode lead 204 includes a plurality of wires (e.g., within an outer sheath) that conductively couple electrodes 206 to one or more current sources within cochlear implant 202. For example, if there are n electrodes 206 on electrode lead 204 and n current sources within cochlear implant 202, there may be n separate wires within electrode lead 204 that are configured to conductively connect each electrode 206 to a different one of the n current sources. Exemplary values for n are 8, 12, 16, or any other suitable number.

Electrodes 206 are located on at least a distal portion of electrode lead 204. In this configuration, after the distal portion of electrode lead 204 is inserted into the cochlea, electrical stimulation may be applied by way of one or more of electrodes 206 to one or more intracochlear locations. One or more other electrodes (e.g., including a ground electrode, not explicitly shown) may also be disposed on other parts of electrode lead 204 (e.g., on a proximal portion of electrode lead 204) to, for example, provide a current return path for stimulation current applied by electrodes 206 and to remain external to the cochlea after the distal portion of electrode lead 204 is inserted into the cochlea. Additionally or alternatively, a housing of cochlear implant 202 may serve as a ground electrode for stimulation current applied by electrodes 206.

Processing unit 208 may be configured to interface with (e.g., control and/or receive data from) cochlear implant 202. For example, processing unit 208 may transmit commands (e.g., stimulation parameters and/or other types of operating parameters in the form of data words included in a forward telemetry sequence) to cochlear implant 202 by way of communication link 210. Processing unit 208 may additionally or alternatively provide operating power to cochlear implant 202 by transmitting one or more power signals to cochlear implant 202 by way of communication link 210. Processing unit 208 may additionally or alternatively receive data from cochlear implant 202 by way of communication link 210. Communication link 210 may be implemented by any suitable number of wired and/or wireless bidirectional and/or unidirectional links.

As shown, processing unit 208 includes a memory 212 and a processor 214 configured to be selectively and communicatively coupled to one another. In some examples, memory 212 and processor 214 may be distributed between multiple devices and/or multiple locations as may serve a particular implementation.

Memory 212 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 212 may maintain (e.g., store) executable data used by processor 214 to perform one or more of the operations described herein. For example, memory 212 may store instructions 216 that may be executed by processor 214 to perform any of the operations described herein. Instructions 216 may be implemented by any suitable application, program (e.g., sound processing program), software, code, and/or other executable data instance. Memory 212 may also maintain any data received, generated, managed, used, and/or transmitted by processor 214.

Processor 214 may be configured to perform (e.g., execute instructions 216 stored in memory 212 to perform) various operations with respect to cochlear implant 202.

To illustrate, processor 214 may be configured to control an operation of cochlear implant 202. For example, processor 214 may receive an audio signal (e.g., by way of a microphone communicatively coupled to processing unit

208, a wireless interface (e.g., a Bluetooth interface), and/or a wired interface (e.g., an auxiliary input port)). Processor 214 may process the audio signal in accordance with a sound processing program (e.g., a sound processing program stored in memory 212) to generate appropriate stimulation parameters. Processor 214 may then transmit the stimulation parameters to cochlear implant 202 to direct cochlear implant 202 to apply electrical stimulation representative of the audio signal to the recipient.

In some implementations, processor 214 may also be configured to apply acoustic stimulation to the recipient. For example, a receiver (also referred to as a loudspeaker) may be optionally coupled to processing unit 208. In this configuration, processor 214 may deliver acoustic stimulation to the recipient by way of the receiver. The acoustic stimulation may be representative of an audio signal (e.g., an amplified version of the audio signal), configured to elicit an evoked response within the recipient, and/or otherwise configured. In configurations in which processor 214 is configured to both deliver acoustic stimulation to the recipient and direct cochlear implant 202 to apply electrical stimulation to the recipient, cochlear implant system 200 may be referred to as a bimodal hearing system and/or any other suitable term.

Processor 214 may be additionally or alternatively configured to receive and process data generated by cochlear implant 202. For example, processor 214 may receive data representative of a signal recorded by cochlear implant 202 using one or more electrodes 206 and, based on the data, adjust one or more operating parameters of processing unit 208. Additionally or alternatively, processor 214 may use the data to perform one or more diagnostic operations with respect to cochlear implant 202 and/or the recipient.

Other operations may be performed by processor 214 as may serve a particular implementation. In the description provided herein, any references to operations performed by processing unit 208 and/or any implementation thereof may be understood to be performed by processor 214 based on instructions 216 stored in memory 212.

Figure 3:
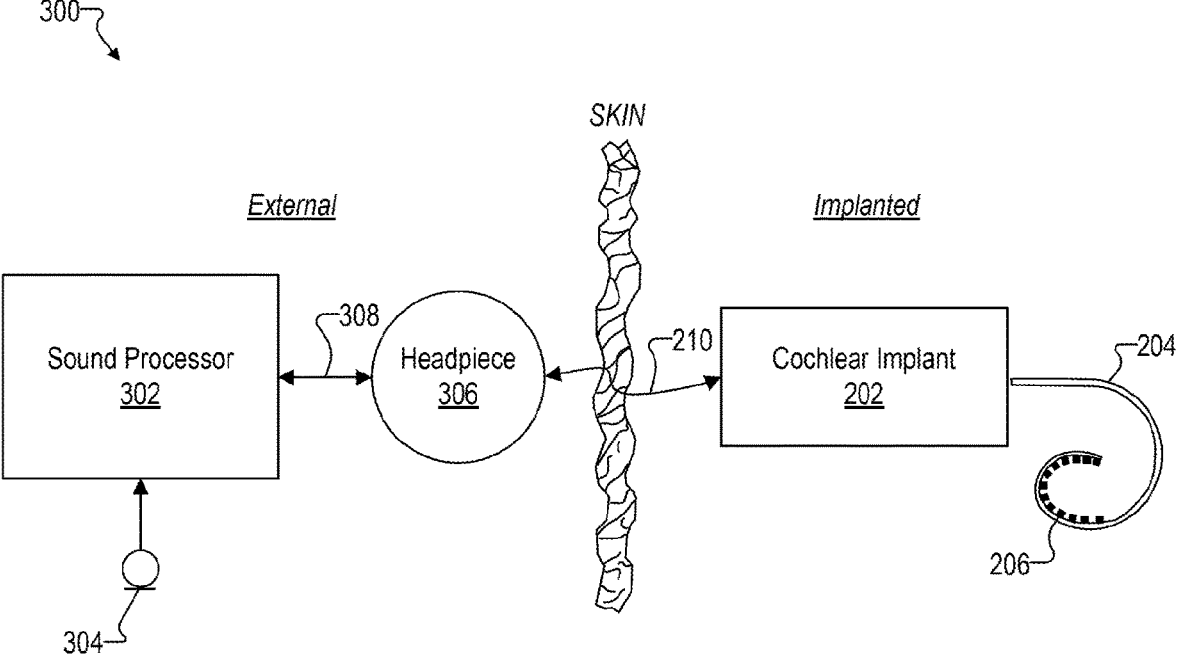
FIG. 3 shows an exemplary configuration of the cochlear implant system of FIG. 2.

Processing unit 208 may be implemented by one or more devices configured to interface with cochlear implant 202. To illustrate, FIG. 3 shows an exemplary configuration 300 of cochlear implant system 200 in which processing unit 208 is implemented by a sound processor 302 configured to be located external to the recipient. In configuration 300, sound processor 302 is communicatively coupled to a microphone 304 and to a headpiece 306 that are both configured to be located external to the recipient.

Sound processor 302 may be implemented by any suitable device that may be worn or carried by the recipient. For example, sound processor 302 may be implemented by a BTE unit configured to be worn behind and/or on top of an ear of the recipient. Additionally or alternatively, sound processor 302 may be implemented by an off-the-ear unit (also referred to as a body worn device) configured to be worn or carried by the recipient away from the ear. Additionally or alternatively, at least a portion of sound processor 302 is implemented by circuitry within headpiece 306.

Microphone 304 is configured to detect one or more audio signals (e.g., that include speech and/or any other type of sound) in an environment of the recipient. Microphone 304 may be implemented in any suitable manner. For example, microphone 304 may be implemented by a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 302. Additionally or alternatively, microphone 304 may be implemented by one or more microphones in or on headpiece 306, one or more microphones in or on a housing of sound processor 302, one or more beam-forming microphones, and/or any other suitable microphone as may serve a particular implementation.

Headpiece 306 may be selectively and communicatively coupled to sound processor 302 by way of a communication link 308 (e.g., a cable or any other suitable wired or wireless communication link), which may be implemented in any suitable manner. Headpiece 306 may include an external antenna (e.g., a coil and/or one or more wireless communication components) configured to facilitate selective wireless coupling of sound processor 302 to cochlear implant 202. Headpiece 306 may additionally or alternatively be used to selectively and wirelessly couple any other external device to cochlear implant 202. To this end, headpiece 306 may be configured to be affixed to the recipient's head and positioned such that the external antenna housed within headpiece 306 is communicatively coupled to a corresponding implantable antenna (which may also be implemented by a coil and/or one or more wireless communication components) included within or otherwise connected to cochlear implant 202. In this manner, stimulation parameters and/or power signals may be wirelessly and transcutaneously transmitted between sound processor 302 and cochlear implant 202 by way of a wireless communication link 310.

In configuration 300, sound processor 302 may receive an audio signal detected by microphone 304 by receiving a signal (e.g., an electrical signal) representative of the audio signal from microphone 304. Sound processor 302 may additionally or alternatively receive the audio signal by way of any other suitable interface as described herein. Sound processor 302 may process the audio signal in any of the ways described herein and transmit, by way of headpiece 306, stimulation parameters to cochlear implant 202 to direct cochlear implant 202 to apply electrical stimulation representative of the audio signal to the recipient.

In an alternative configuration, sound processor 302 may be implanted within the recipient instead of being located external to the recipient. In this alternative configuration, which may be referred to as a fully implantable configuration of cochlear implant system 200, sound processor 302 and cochlear implant 202 may be combined into a single device or implemented as separate devices configured to communicate one with another by way of a wired and/or wireless communication link. In a fully implantable implementation of cochlear implant system 200, headpiece 306 may not be included and microphone 304 may be implemented by one or more microphones implanted within the recipient, located within an ear canal of the recipient, and/or external to the recipient.

Figure 4:
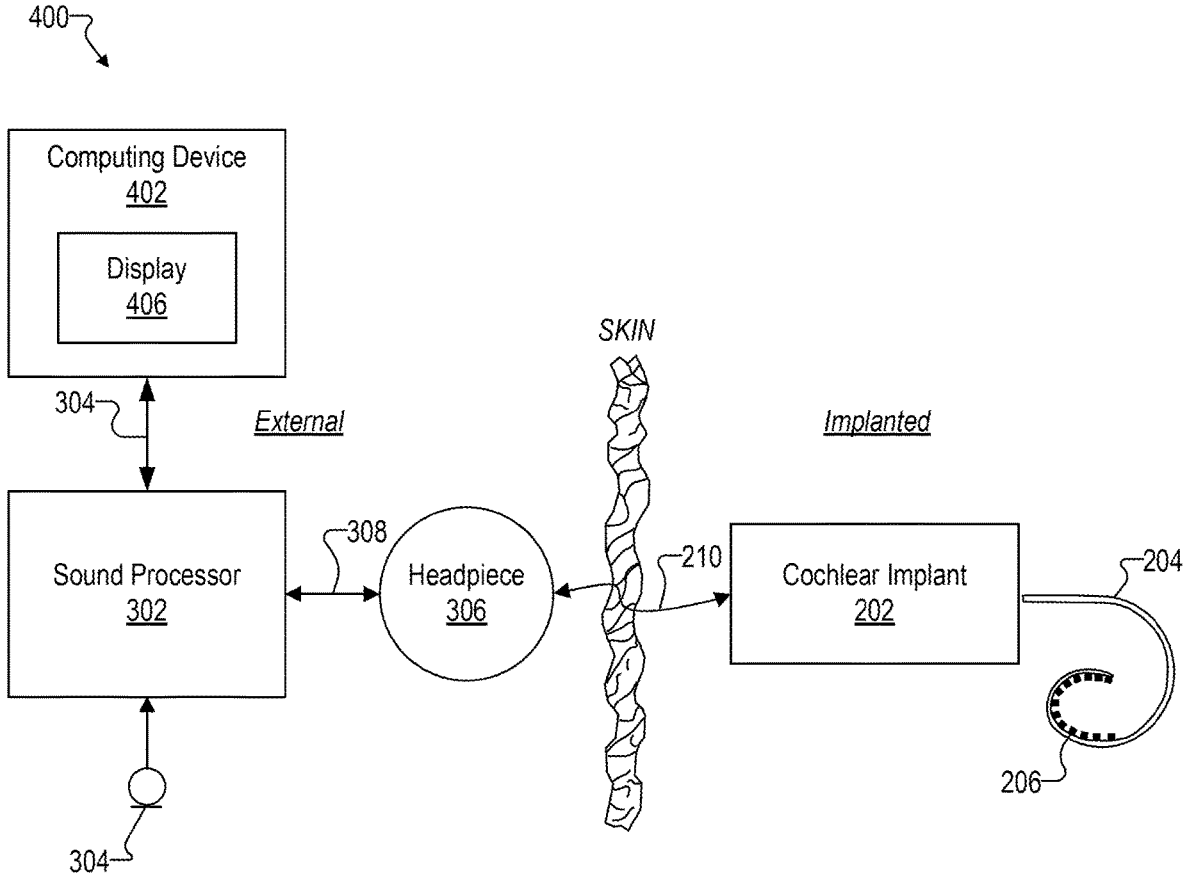
FIG. 4 shows another exemplary configuration of the cochlear implant system of FIG. 2.

FIG. 4 shows an exemplary configuration 400 of cochlear implant system 200 in which processing unit 208 is implemented by a combination of sound processor 302 and a computing device 402 configured to communicatively couple to sound processor 302 by way of a communication link 404, which may be implemented by any suitable wired or wireless communication link.

Computing device 402 may be implemented by any suitable combination of hardware and software. To illustrate, computing device 402 may be implemented by a mobile device (e.g., a mobile phone, a laptop, a tablet computer, etc.), a desktop computer, and/or any other suitable computing device as may serve a particular implementation. As an example, computing device 402 may be implemented by a mobile device configured to execute an application (e.g., a "mobile app") that may be used by a user (e.g., the recipient, a clinician, and/or any other user) to control one or more settings of sound processor 302 and/or cochlear implant 202 and/or perform one or more operations (e.g., diagnostic operations) with respect to data generated by sound processor 302 and/or cochlear implant 202.

In some examples, computing device 402 may be configured to control an operation of cochlear implant 202 by transmitting one or more commands to cochlear implant 202 by way of sound processor 302. Likewise, computing device 402 may be configured to receive data generated by cochlear implant 202 by way of sound processor 302. Alternatively, computing device 402 may interface with (e.g., control and/or receive data from) cochlear implant 202 directly by way of a wireless communication link between computing device 402 and cochlear implant 202. In some implementations in which computing device 402 interfaces directly with cochlear implant 202, sound processor 302 may or may not be included in cochlear implant system 200.

Computing device 402 is shown as having an integrated display 406. Display 406 may be implemented by a display screen, for example, and may be configured to display content generated by computing device 402. Additionally or alternatively, computing device 402 may be communicatively coupled to an external display device (not shown) configured to display the content generated by computing device 402.

In some examples, computing device 402 represents a fitting device configured to be selectively used (e.g., by a clinician) to fit sound processor 302 and/or cochlear implant 202 to the recipient. In these examples, computing device 402 may be configured to execute a fitting program configured to set one or more operating parameters of sound processor 302 and/or cochlear implant 202 to values that are optimized for the recipient. As such, in these examples, computing device 402 may not be considered to be part of cochlear implant system 200. Instead, computing device 402 may be considered to be separate from cochlear implant system 200 such that computing device 402 may be selectively coupled to cochlear implant system 200 when it is desired to fit sound processor 302 and/or cochlear implant 202 to the recipient.

Returning to FIG. 1, memory 104 and processor 106 of hearing device 102 may each include or be implemented by hardware and/or software components (e.g., processors, memories, communication interfaces, instructions stored in memory for execution by the processors, etc.). In some examples, memory 104 and processor 106 may be housed within or form part of an implanted component of hearing device 102 (e.g., a fully implanted housing) within the recipient. In other examples, memory 104 and processor 106 may be externally located (e.g., in a BTE component). In some alternative examples, memory 104 and processor 106 may be distributed between multiple devices (e.g., multiple hearing devices in a binaural hearing system) and/or multiple locations as may serve a particular implementation.

Memory 104 may maintain (e.g., store) executable data used by processor 106 to perform any of the operations associated with hearing device monitoring system 100 described herein. For example, memory 104 may store instructions 110 that may be executed by processor 106 to perform any of the operations associated with hearing device monitoring system 100 described herein. Instructions 110 may be implemented by any suitable application, software, code, and/or other executable data instance.

Memory 104 may also maintain any data received, generated, managed, used, and/or transmitted by processor 106. For example, memory 104 may maintain any suitable data associated with triggering events, operational effectiveness states, notifications that may be provided to a recipient, user interface content, information associated with corrective measures to address effects of triggering events, sensor data, baseline signal data, etc. Memory 104 may maintain additional or alternative data in other implementations.

Processor 106 is configured to perform any suitable processing operation that may be associated with hearing device monitoring system 100. For example, when hearing device 102 is implemented by a hearing aid device, such processing operations may include monitoring ambient sound and/or representing sound to a user via an in-ear receiver. In examples where hearing device 102 is implemented as part of a cochlear implant system, such processing operations may include directing a cochlear implant to generate and apply electrical stimulation representative of one or more audio signals (e.g., one or more audio signals detected by a microphone, input by way of an auxiliary audio input port, etc.) to one or more stimulation sites associated with an auditory pathway (e.g., the auditory nerve) of a user. Processor 106 may be implemented by any suitable combination of hardware and software.

In addition, processor 106 is configured to perform any suitable processing operation associated with determining effects of triggering event that occurs during use of hearing device 102. For example, processor 106 may control operation of sensors 108 or use sensor data output by sensors 108 in any suitable manner to detect occurrence of a triggering event.

Sensors 108 may include any suitable sensor that may be used to provide sensor data associated with triggering events such as those described herein. For example, sensors 108 may include, but are not limited to, a microphone (e.g., microphone 304), a temperature sensor, an accelerometer, a strain gauge, a piezoelectric transducer, a pulse oximetry sensor, heart rate sensor, an optical spectroscopy sensor (e.g., to detect chemical markers), an electrostatic discharge detection circuit, implant electrodes (e.g., electrodes 206), external electrodes (e.g., that are external to the recipient), an electroencephalogram ("EEG") sensor, an electrocardiogram ("ECG") sensor, an electrooculogram ("EOG") sensor, and/or any other suitable sensor. In certain examples, one or more of sensors 108 or each of sensors 108 may be included as part of hearing device 102. In certain alternative examples, one or more of sensors 108 may be included as part of an external device that is external to hearing device 102 but that is in communication with hearing device 102. Such an external device may be implanted within the recipient or may be external to the recipient. For example, one or more of sensors 108 may be included as part of a mobile device (e.g., a smartphone, a smartwatch, a health monitoring device, etc.) that may be included as part of or communicatively coupled to hearing device monitoring system 100. Although a plurality of sensors 108 are shown in FIG. 1, it is understood that only one sensor may be included as part of hearing device monitoring system 100 in certain implementations.

Hearing device monitoring system 100 ("system 100") (e.g., processor 106 of hearing device 102) may perform various operations to determine an operational effectiveness state of a hearing device after occurrence of a triggering event. For example, system 100 may compare a signal recorded after occurrence of a triggering event to a baseline signal recorded prior to the triggering event and determine, based on the comparing of the signal to the baseline signal, an operational effectiveness state of the hearing device. These and other operations that may be performed by system 100 are described herein.

To facilitate determining whether a triggering event such as those described herein has occurred, system 100 may obtain sensor data output from one or more of sensors 108 while hearing device 102 is in use by a recipient. System 100 may obtain the sensor data in any suitable manner. For example, in certain implementations, sensors 108 may be configured to output sensor data any time the sensor data satisfies a predefined condition. To illustrate, sensor 108-1 may correspond to an electrostatic discharge detection circuit that is configured to output sensor data each time hearing device 102 experiences an electrostatic discharge above a predefined level. Alternatively, system 100 may continually monitor sensor data output by sensors 108 to detect a triggering event.

Based on the sensor data, system 100 may detect a triggering event that occurs during use of hearing device 102. System 100 may detect a triggering event in any suitable manner. For example, sensor 108-1 may correspond to an accelerometer and sensor 108-2 may correspond to a microphone (e.g., microphone 304). If sensor data output by sensor 108-1 has an acceleration value above a predefined threshold, system 100 may detect that a triggering event has occurred in the form of a mechanical impact experienced by the recipient. On the other hand, if sensor data output by sensor 108-2 has a loudness level above a predefined threshold (e.g., an abrupt sound possibly indicative of an accident), system 100 may detect that a triggering event has occurred.

Based on the detecting of the triggering event, system 100 may apply stimulation to the recipient. System 100 may apply stimulation to the recipient in any suitable manner. For example, exemplary stimulation that may be applied by system 100 may include single/multiple electrode pulses or pulse trains provided by way of one or more electrodes (e.g., electrodes 206), a pre-determined response across electrodes for a signal such as a tone sweep, modulated tones/noises, speech-like sounds, etc., acoustic stimulation (e.g., tone sweep, modulated tones/noises, speech-like sounds, etc.), and/or any combination thereof.

System 100 may apply the stimulation to the recipient at any suitable time as may serve a particular implementation. For example, system 100 may apply the stimulation either immediately after the detecting of the triggering event or within a predefined amount of time after the detecting of the triggering event. In certain examples, system 100 may apply the stimulation to the recipient periodically after occurrence of the triggering event.

After system 100 applies the stimulation to the recipient, system 100 may detect a signal that occurs in response to the stimulation. System 100 may detect any suitable signal in any suitable manner. For example, in certain implementations, system 100 may detect a signal recorded by an electrode (e.g., one or more of electrodes 206) associated with hearing device 102. In such examples, the signal recorded by the electrode may include electrode impedances, evoked responses, central (cortical) potentials, and/or any other suitable signal. As used herein, an "evoked response" refers to a neural response (e.g., a compound action potential) and/or any other type of physiological response that may occur within a recipient in response to application of stimulation (e.g., by way of electrodes 206).

After system 100 detects the signal, system 100 may compare the signal to a baseline signal recorded by an electrode prior to a triggering event. The baseline signal may correspond to a previously recorded signal that may be indicative of normal operation of hearing device 102. In certain examples, the baseline signal may correspond to a baseline evoked response.

System 100 may record a baseline signal prior to a triggering event in any suitable manner. For example, system 100 may periodically perform a series of measurements to form an individual assessment of hearing device integrity and stimulation effectiveness. In certain examples, system 100 may perform such measurements as part of a hearing device power-up/lock cycle. For example, system 100 may perform measurements to establish a baseline signal that is specific to a given recipient each time hearing device 102 powers on.

System 100 may compare the signal to the baseline signal in any suitable manner using any suitable features or attributes associated with the signal and the baseline signal. For example, system 100 may compare basic response features of the signal to the baseline signal such as differences between peaks and/or troughs of the signals, peak and/or trough latencies of the signals, and/or averages of the signals. Additionally or alternatively, system 100 may compare the signal to the baseline signal using inferred response features such as threshold stimulus levels, response magnitude to fixed stimulus levels, mismatch-negativity, and/or any other suitable inferred response feature. Additionally or alternatively, system 100 may prompt a recipient in any suitable manner for voice feedback regarding the stimulus applied to the recipient to facilitate comparing the signal to the baseline signal.

System 100 may determine, based on the comparing of the signal to the baseline signal, an operational effectiveness state of the hearing device. This may be accomplished in any suitable manner. For example, system 100 may analyze the signal and the baseline signal and determine that the peaks and/or troughs of the signal match or are within some pre-defined degree of similarity to the peaks and/or troughs of the baseline signal. In such examples, system 100 may determine that hearing device 102 is operating correctly and that the triggering event has not negatively affected hearing device 102. Alternatively, system 100 may analyze the signal and the baseline signal and determine, for example, that the peaks and/or troughs of the signal do not match or are not within some pre-defined degree of similarity to the peaks and/or troughs of the baseline signal. In such an example, system 100 may determine that hearing device 102 is not operating correctly and that the triggering event has potentially caused damage to hearing device 102 and/or the recipient.

In certain examples, system 100 may be configured to compare a signal obtained by an implanted sensor and a signal obtained by an external sensor that is external to a recipient to facilitate determining an operational effectiveness state of hearing device 102. For example, an electrode used to detect a signal that occurs in response to the stimulation may be implanted within a recipient. An additional sensor that is external to the recipient may be used to record an additional signal in response to the stimulation. In such an example, the additional sensor may correspond to an additional electrode that may be mounted on an exterior surface of, for example, an ITE unit, a BTE unit, or any other suitable device that may be part of system 100 or that may be communicatively coupled to system 100. System 100 may compare the signal to the additional signal in any suitable manner, such as described herein. System 100 may then use the comparison of the signal to the additional signal to further determine the operational effectiveness state of hearing device 102.

In certain examples, system 100 may also compare the additional signal to the baseline signal. In such examples, system 100 may use the comparison of the signal to the baseline signal and the comparison of the additional signal to the baseline signal to determine the operational effectiveness state of hearing device 102.

In certain examples, system 100 may perform an action to correct or otherwise address effects that may be caused by a triggering event. System 100 may perform any suitable action to correct or otherwise address effects of a triggering event as may serve a particular implementation. To illustrate an example, an electrode used to record a signal that occurs in response to stimulation may be included in a plurality of electrodes (e.g., electrodes 206) implanted within the recipient. In such an example, system 100 may determine, based on the operational effectiveness of hearing device 102, that at least one electrode included in the plurality of electrodes is non-operational. For example, the at least one electrode may have been damaged as a result of the triggering event. Additionally or alternatively, the tissue adjacent to the at least one electrode may have been damaged causing the at least one electrode to not function properly. To address this, system 100 may perform any suitable action to compensate for the at least one electrode being non-operational. For example, in certain implementations, system 100 may remap input frequencies to be provided to other electrodes included in the plurality of electrodes instead of to the at least one electrode.

In certain examples, the action performed by system 100 may include shutting down or otherwise disabling one or more components of hearing device 102. For example, system 100 may determine that the triggering event caused damage to processor 106. In such an example, system 100 may shut down processor 106 in any suitable manner. Additionally or alternatively, the action may include system 100 automatically shutting down and restarting hearing device 102 in response to a triggering event.

In certain examples, system 100 may be configured to provide a notification to a recipient regarding an operational effectiveness state of hearing device 102. Such a notification may be provided at any suitable time to a recipient. In certain examples, system 100 may provide a notification either immediately after or within a predefined time period after detecting a triggering event. In so doing, the recipient may be quickly apprised of whether the triggering event caused damage to hearing device 102 and/or the recipient or otherwise caused hearing device 102 to operate improperly.

System 100 may provide a notification to a recipient in any suitable manner. For example, system 100 may cause hearing device 102 to provide an audio notification in the form of a voice recording perceivable by the recipient. Examples of such an audio notification may include, but are not limited to, voice messages indicating that "your hearing device is operating properly," "the operation of your hearing device has been compromised," "your hearing device has been damaged," "please visit a clinician to address issues with your hearing device," "an impact has been detected, we will let you know if there is an issue," etc.

Additionally or alternatively, system 100 may provide a text notification, a graphical notification, an email notification, and/or any other suitable notification to a user regarding the operational effectiveness state of hearing device 102. In certain examples, such notifications may be provided by way of a computing device included as part of or communicatively coupled to system 100. For example, system 100 may provide a notification to a mobile device (e.g., a smartphone) to be presented to the recipient (e.g., by way of a display screen of the mobile device).

In certain examples, the notification may inform a recipient regarding action(s) already taken by system 100 to address effects caused by a triggering event. For example, system 100 may provide a notification indicating that operating parameters of hearing device 102 have been automatically adjusted to address effects of a triggering event and that hearing device 102 is now operating properly.

In certain examples, effects of a triggering event may not manifest themselves immediately. Rather, a measurement schedule and final assessment of the operational effectiveness state of hearing device 102 may extend a predefined time period after occurrence of the triggering event. In such examples, system 100 may evaluate the operational effectiveness state of hearing device 102 over the course of the predefined time period. For example, hearing device monitoring system may monitor the operational effectiveness state over a period of several weeks to determine effects of the triggering event on hearing device 102 and any trends in operation of hearing device 102. During the predefined time period, system 100 may apply a series of stimulation to the recipient. System 100 may then detect a series of signals that occur in response to stimulation applied during a predefined time period. In such examples, the comparing of the signal to the baseline signal may include comparing each signal included in the series of signals to a baseline signal recorded prior to the triggering event. In examples where effects of a triggering event may be evaluated over a period of time, a series of notifications may be provided to the recipient over the course of the period of time to update the recipient regarding the operational effectiveness state of hearing device 102.

In certain examples, system 100 may be configured to determine an operational effectiveness state based on input provided by a recipient. For example, after a recipient experiences a triggering event, the recipient may provide any suitable manual input by way of an interface associated with hearing device 102 to instruct system 100 to check for effects associated with the triggering event. In response, system 100 may determine the operational effectiveness state and perform any suitable action such as those described herein. For example, system 100 may provide any suitable notification informing the recipient regarding effects, possible damage, actions taken, actions that need to be taken, whether issues associated with the triggering event have been resolved, whether effects associated with the triggering event were only temporary, and/or any other suitable notification.

Figure 5:
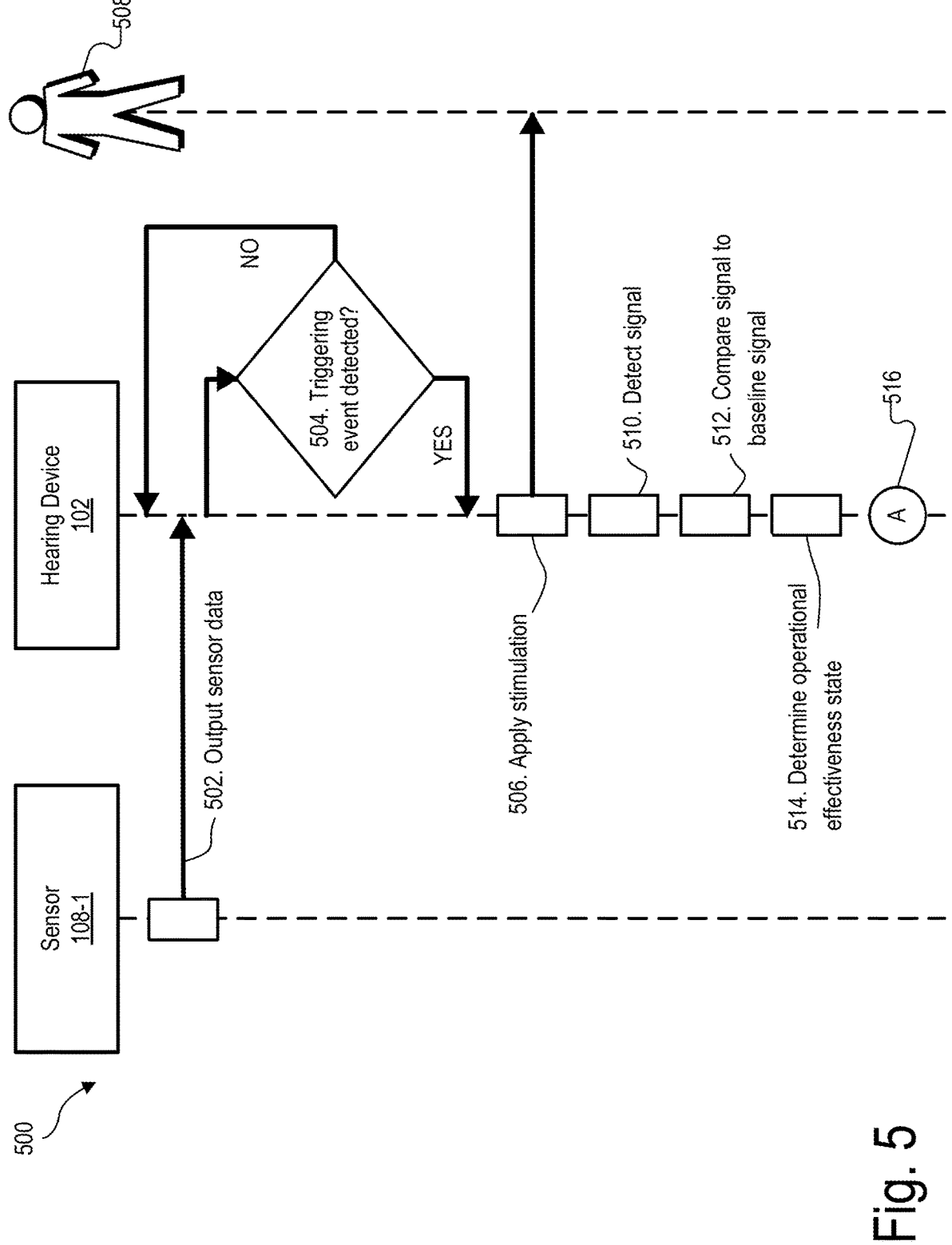
FIGS. 5 and 6 show exemplary flow diagrams depicting operations that may be performed by the hearing device monitoring system of FIG. 1 according to principles described herein.

FIG. 5 shows an exemplary flow diagram 500 with exemplary operations that may be performed by system 100 according to principles described herein. As shown in FIG. 5, sensor 108-1 may output sensor data at operation 502.

At operation 504, hearing device 102 (e.g., processor 106) may determine whether a triggering event has been detected. If the answer at operation 504 is "NO," the flow may return to a state in which hearing device 102 is configured to detect additional sensor data output by sensor 108-1. If the answer at operation 504 is "YES," hearing device 102 may cause stimulation to be applied at operation 506 to recipient 508. The stimulation may be applied at operation 506 in any suitable manner, such as described herein.

At operation 510, hearing device 102 may detect a signal that occurs in response to the stimulation. In certain examples, the signal may be recorded by an electrode associated with hearing device 102.

At operation 512, hearing device 102 may compare the signal to a baseline signal recorded prior to the triggering event. Hearing device 102 may compare the signal to the baseline signal in any suitable manner, such as described herein.

At operation 514, hearing device 102 may determine, based on the comparing of the signal to the baseline signal, an operational effectiveness state of hearing device 102.

Figure 6:
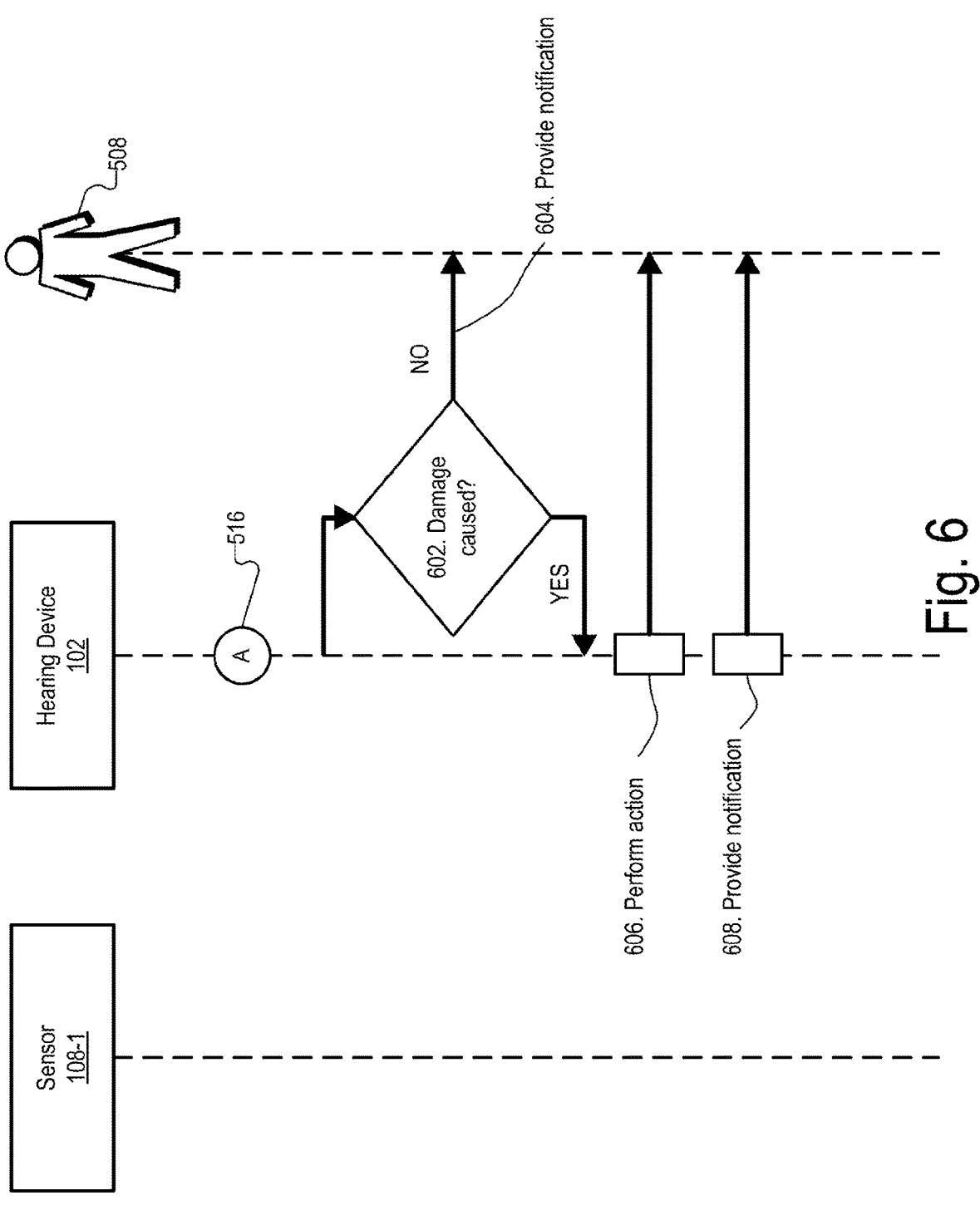

A circle 516 labeled "A" in FIG. 5 represents a starting point for flowchart 600 shown in FIG. 6, which shows additional operations that may be performed by hearing device 102 in certain implementations. As shown in FIG. 6, at operation 602, hearing device 102 may determine whether damage was caused because of the triggering event.

If the answer at operation 602 is "NO," hearing device 102 may provide any suitable notification to recipient 508 at operation 604 indicating that no damage was caused. For example, hearing device may provide an audio notification, a text message, an email, etc. informing recipient 508 that no damage was caused.

If the answer at operation 602 is "YES," hearing device 102 may perform an action at operation 606 to address the damage caused by the triggering event. For example, hearing device 102 may automatically adjust a setting and/or function of hearing device 102 to correct for the damage caused. In certain examples, the action performed at operation 604 may include hearing device 102 remapping input frequencies to be provided to other electrodes included in a plurality of electrodes of hearing device 102 instead to an electrode that may be damaged or otherwise not operating properly.

At operation 608, hearing device 102 may provide a notification to recipient 508 in any suitable manner, such as described herein, regarding the damage. Such a notification may include information indicating, for example, what has been done to address the damage, what recipient 508 may need to do to address the damage, and/or any other suitable steps to address the damage.

In certain examples, an action such as that performed at operation 606 may include system 100 automatically transmitting information representative of an operational effectiveness state of a hearing device to an external device/entity that is external to system 100 for processing and/or analysis. For example, system 100 may direct a communication interface of system 100 to automatically (e.g., without requiring input from the recipient) transmit the information at any suitable time to one or more external devices (e.g., a smartphone, a tablet computer, a fitting system, a clinician facility, etc.) and/or entities communicatively coupled to hearing system for processing and/or analysis.

Figure 7:
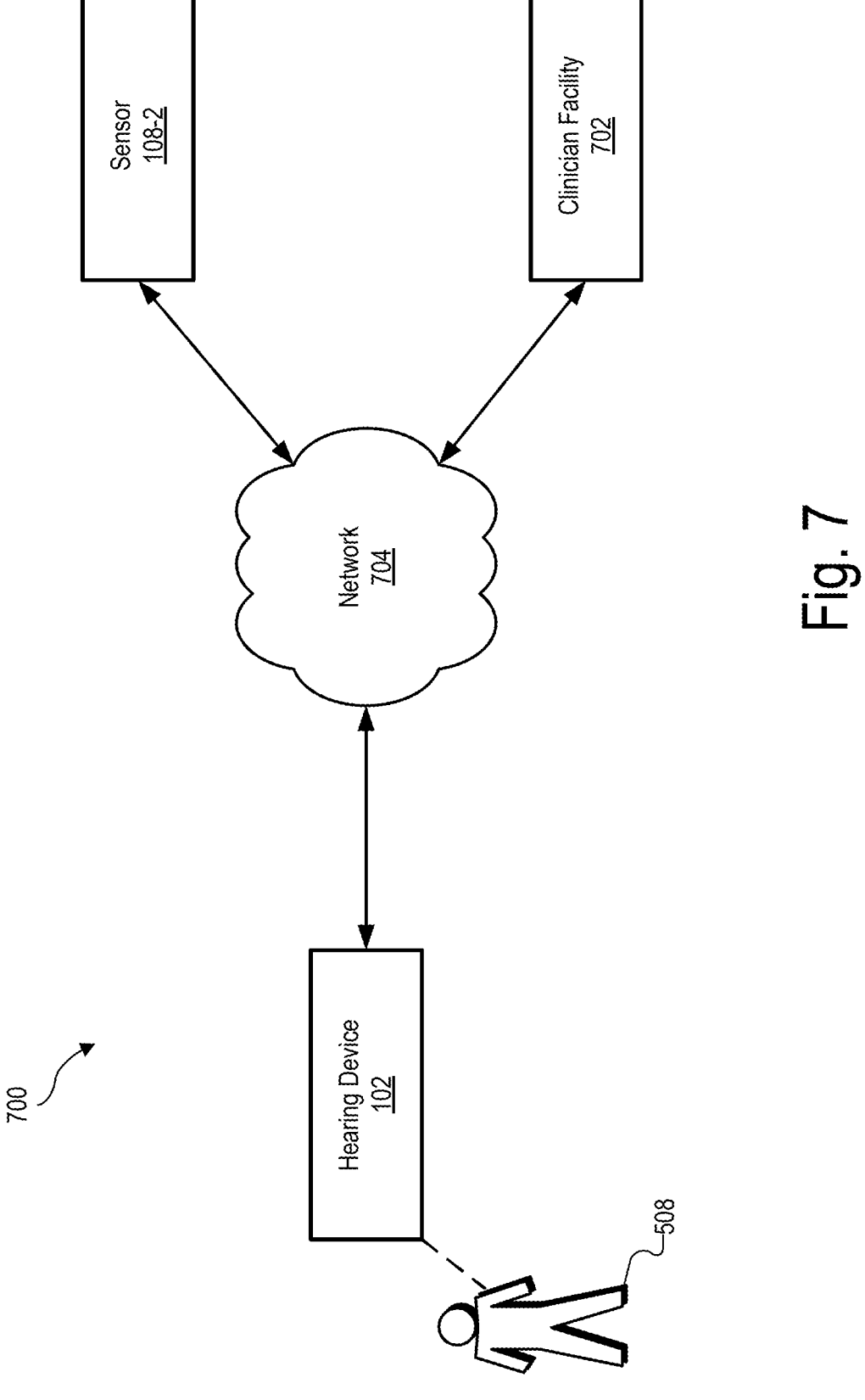
FIG. 7 shows an exemplary configuration of the hearing device monitoring system of FIG. 1 according to principles described herein.

System 100 may transmit information associated with an operational effectiveness state of a hearing device to an entity such as a clinician facility in any suitable manner. To illustrate, FIG. 7 shows an exemplary configuration 700 in which system 100 may be implemented in certain examples. As shown in FIG. 7, hearing device 102 may be connected to a clinician facility 702 and, for example, sensor 108-2 by way of a network 704.

Clinician facility 702 may correspond to any entity that may be configured to analyze and/or process information associated with triggering events and provide support to recipients of hearing device 102 to address effects of the triggering events. In certain examples, clinician facility 702 may correspond to a fitting facility where hearing device 102 may be initially fit and/or adjusted for recipient 508.

Network 704 may include any provider-specific wired or wireless network (e.g., a cable or satellite carrier network or a mobile telephone network), the Internet, a wide area network, or any other suitable network. Data may flow between hearing device 102, sensor 108-2, and clinician facility 702 using any communication technologies, devices, media, and protocols as may serve a particular implementation. For example, hearing device 102, sensor 108-2, and clinician facility 702 may communicate using any suitable communication technologies, devices, media, and/or protocols supportive of data communications, including, but not limited to, socket connections, Ethernet, data bus technologies, data transmission media, communication devices, media streaming technologies (e.g., video streaming technologies), Moving Picture Experts Group ("MPEG") protocols, Transmission Control Protocol ("TCP"), Internet Protocol ("IP"), File Transfer Protocol ("FTP"), Telnet, Hypertext Transfer Protocol ("HTTP"), HTTPS, Session Initiation Protocol ("SIP"), Simple Object Access Protocol ("SOAP"), Extensible Mark-up Language ("XML") and variations thereof, Real-Time Transport Protocol ("RTP"), User Datagram Protocol ("UDP"), Global System for Mobile Communications ("GSM") technologies, Code Division Multiple Access ("CDMA") technologies, Evolution Data Optimized Protocol ("EVDO"), 4G Long Term Evolution ("LTE"), WiMax, Time Division Multiple Access ("TDMA") technologies, radio frequency ("RF") signaling technologies, wireless communication technologies (e.g., Bluetooth, Wi-Fi, etc.), in-band and out-of-band signaling technologies, and other suitable communications technologies. While only one network 704 is shown in FIG. 7, it will be recognized that these devices and systems may intercommunicate by way of multiple and/or different interconnected networks as may serve a particular implementation.

FIG. 8 illustrates an exemplary method for determining effects of a triggering event that occurs during use of a hearing device. While FIG. 8 illustrates exemplary operations according to one embodiment, other embodiments may omit, add to, reorder, and/or modify any of the operations shown in FIG. 8. One or more of the operations shown in FIG. 8 may be performed by a hearing device monitoring system such as system 100, any components included therein, and/or any implementation thereof.

At operation 802, a hearing device monitoring system (e.g., hearing device monitoring system 100) may detect, based on sensor data output by a sensor in communication with a hearing device (e.g., hearing device 102), a triggering event that occurs during use of the hearing device by a recipient of the hearing device. As described herein, the triggering event may be indicative of possible damage to at least one of the hearing device or the recipient. Operation 802 may be performed in any of the ways described herein.

At operation 804, the hearing device monitoring system may apply, in response to the detecting of the triggering event, stimulation to the recipient. Operation 804 may be performed in any of the ways described herein.

At operation 806, the hearing device monitoring system may detect a signal that occurs in response to the stimulation and that is recorded by an electrode associated with the hearing device. Operation 806 may be performed in any of the ways described herein.

At operation 808, the hearing device monitoring system may compare the signal to a baseline signal recorded by the electrode prior to the triggering event. Operation 808 may be performed in any of the ways described herein.

At operation 810, the hearing device monitoring system may determine, based on the comparing of the signal to the baseline signal, an operational effectiveness state of the hearing device. Operation 810 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 9:
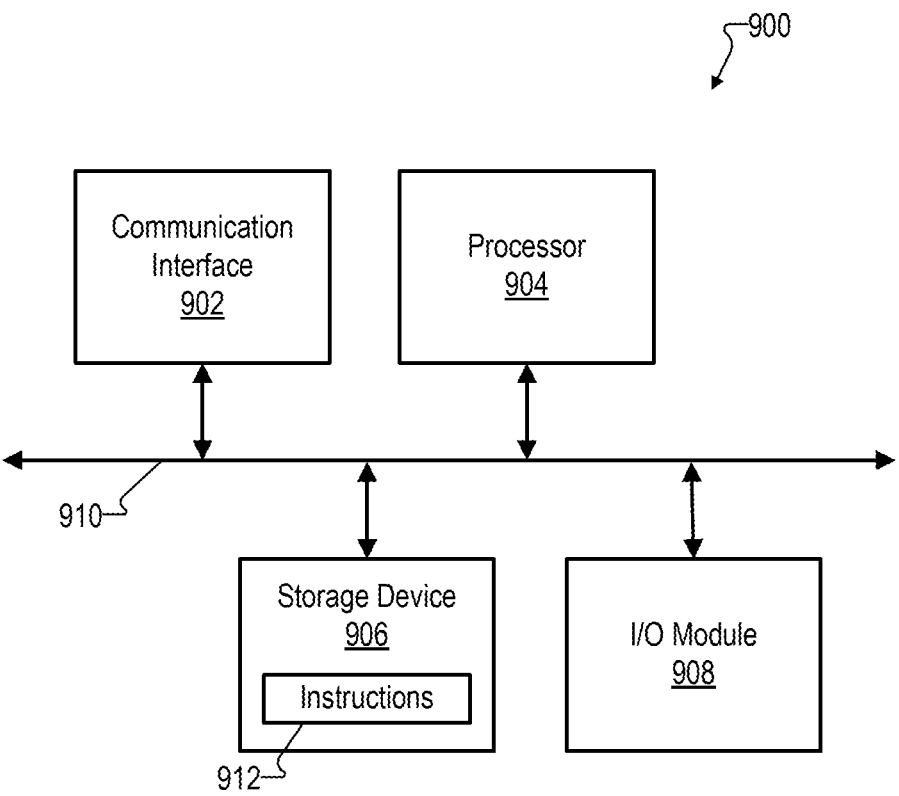
FIG. 9 illustrates an exemplary computing device according to principles described herein.

FIG. 9 illustrates an exemplary computing device 900 that may be specifically configured to perform one or more of the processes described herein. As shown in FIG. 9, computing device 900 may include a communication interface 902, a processor 904, a storage device 906, and an input/output ("I/O") module 908 communicatively connected one to another via a communication infrastructure 910. While an exemplary computing device 900 is shown in FIG. 9, the components illustrated in FIG. 9 are not intended to be limiting. Additional or alternative components may be used in other embodiments. Components of computing device 900 shown in FIG. 9 will now be described in additional detail.

Communication interface 902 may be configured to communicate with one or more computing devices. Examples of communication interface 902 include, without limitation, a wired network interface (such as a network interface card), a wireless network interface (such as a wireless network interface card), a modem, an audio/video connection, and any other suitable interface.

Processor 904 generally represents any type or form of processing unit capable of processing data and/or interpreting, executing, and/or directing execution of one or more of the instructions, processes, and/or operations described herein. Processor 904 may perform operations by executing computer-executable instructions 912 (e.g., an application, software, code, and/or other executable data instance) stored in storage device 906.

Storage device 906 may include one or more data storage media, devices, or configurations and may employ any type, form, and combination of data storage media and/or device. For example, storage device 906 may include, but is not limited to, any combination of the non-volatile media and/or volatile media described herein. Electronic data, including data described herein, may be temporarily and/or permanently stored in storage device 906. For example, data representative of computer-executable instructions 912 configured to direct processor 904 to perform any of the operations described herein may be stored within storage device 906. In some examples, data may be arranged in one or more databases residing within storage device 906.

I/O module 908 may include one or more I/O modules configured to receive user input and provide user output. I/O module 908 may include any hardware, firmware, software, or combination thereof supportive of input and output capabilities. For example, I/O module 908 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 908 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 908 is configured to provide graphical data to a display for presentation to a user. The graphical data may be representative of one or more graphical user interfaces and/or any other graphical content as may serve a particular implementation.

In some examples, any of the systems, computing devices, and/or other components described herein may be implemented by computing device 900. For example, memory 104 and/or memory 212 may be implemented by storage device 906, and processor 106 and/or processor 214 may be implemented by processor 904.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a sensor configured to output sensor data; and
a hearing device comprising an electrode and a processor configured to:
record a baseline signal using the electrode of the hearing device;
detect, based on the sensor data, a triggering event that occurs during use of the hearing device by a recipient of the hearing device, the triggering event indicative of possible damage to at least one of the hearing device or the recipient;
apply, in response to the detecting of the triggering event, stimulation to the recipient;
detect a signal that occurs in response to the stimulation and that is recorded by the electrode of the hearing device;
compare the signal to the baseline signal recorded by the electrode prior to the triggering event; and
determine, based on the comparing of the signal to the baseline signal, an operational effectiveness state of the hearing device,
wherein the sensor is configured to be external to the recipient of the hearing device during use of the hearing device.

2. The system of claim 1, wherein the signal corresponds to an evoked response and the baseline signal corresponds to a baseline evoked response recorded by the electrode prior to the triggering event.

3. The system of claim 1, wherein:
the applying of the stimulation includes applying the stimulation multiple times during a predefined time period;
the detecting of the signal includes detecting a series of signals that occur in response to the stimulation during the predefined time period;
the comparing of the signal includes comparing each signal included in the series of signals to the baseline signal; and
the determining of the operational effectiveness state is based on the comparing of each signal included in the series of signals to the baseline signal.

4. The system of claim 1, further comprising an additional sensor that is associated with the hearing device and that is external to the recipient, wherein:
the electrode is configured to be implanted within the recipient; and
the processor is further configured to:
detect an additional signal that occurs in response to the stimulation and that is recorded by the additional sensor; and
compare the signal to the additional signal,
wherein the determining of the operational effectiveness state of the hearing device is further based on the comparing of the signal to the additional signal.

5. The system of claim 1, wherein:
the hearing device comprises a plurality of electrodes configured to be implanted within the recipient;
the electrode is included in the plurality of electrodes; and
the processor is further configured to:
determine, based on the operational effectiveness state of the hearing device, that at least one electrode included in the plurality of electrodes is non-operational; and
perform an action to compensate for the at least one electrode being non-operational.

6. The system of claim 5, wherein the performing of the action includes remapping input frequencies to be provided to other electrodes included in the plurality of electrodes instead of to the at least one electrode.

7. The system of claim 1, wherein the operational effectiveness state of the hearing device is indicative of damage to at least one of the hearing device or the recipient as a result of the triggering event.

8. The system of claim 1, wherein the processor is further configured to provide, based on the determined operational effectiveness state, a notification to the recipient regarding the triggering event.

9. The system of claim 1, wherein the processor is further configured to automatically transmit information representative of the operational effectiveness state of the hearing device to a computing device remote from the system for analysis.

10. The system of claim 1, wherein the sensor is included as part of the hearing device.

11. The system of claim 1, further comprising an external device that includes the sensor and that is external to the hearing device and is in communication with the hearing device.

12. A hearing device comprising:
an electrode;
a sensor that is configured to be external to a recipient of the hearing device during use of the hearing device;
a memory storing instructions; and
a processor configured to execute the instructions to:

record a baseline signal using the electrode of the
hearing device;

detect, based on sensor data output by the sensor, a
triggering event that occurs during use of the hearing
device by the recipient of the hearing device, the
triggering event indicative of possible damage to at
least one of the hearing device or the recipient;

apply, in response to the detecting of the triggering
event, stimulation to the recipient;

detect a signal that occurs in response to the stimulation
and that is recorded by the electrode of the hearing
device;

compare the signal to the baseline signal recorded by
the electrode prior to the triggering event; and determine, based on the comparing of the signal to the
baseline signal, an operational effectiveness state of
the hearing device.

13. The hearing device of claim 12, wherein the signal
corresponds to an evoked response and the baseline signal
corresponds to a baseline evoked response recorded by the
electrode prior to the triggering event.

14. The hearing device of claim 12, wherein the hearing device comprises a plurality of electrodes
configured to be implanted within the recipient;

the electrode is included in the plurality of electrodes; and the processor is further configured execute the instruc-
tions to:

determine, based on the operational effectiveness state
of the hearing device, that at least one electrode
included in the plurality of electrodes is non-opera-
tional; and perform an action to compensate for the at least one
electrode being non- operational.

15. The hearing device of claim 14, wherein the perform-
ing of the action includes remapping input frequencies to be
provided to other electrodes included in the plurality of
electrodes instead of to the at least one electrode.

16. The hearing device of claim 12, wherein the processor
is further configured to execute the instructions to provide,
based on the determined operational effectiveness state, a
notification to the recipient regarding the triggering event.

17. A method comprising:

recording, by a hearing device monitoring system, a
baseline signal using an electrode of a hearing device;

detecting, by the hearing device monitoring system and
using a sensor that is in communication with the
hearing device and that is configured to be external to
a recipient of the hearing device during use of the
hearing device, sensor data;

detecting, by the hearing device monitoring system based
on the sensor data output by the sensor, a triggering
event that occurs during use of the hearing device by
the recipient of the hearing device, the triggering event
indicative of possible damage to at least one of the
hearing device or the recipient;

applying, by the hearing device monitoring system in
response to the detecting of the triggering event, stimu-
lation to the recipient;

detecting, by the hearing device monitoring system, a
signal that occurs in response to the stimulation and
that is recorded by an electrode associated with the
hearing device;

comparing, by the hearing device monitoring system, the
signal to the baseline signal recorded by the electrode
prior to the triggering event; and determining, by the hearing device monitoring system
based on the comparing of the signal to the baseline
signal, an operational effectiveness state of the hearing
device.

18. The method of claim 17, wherein the signal corre-
sponds to an evoked response and the baseline signal
corresponds to a baseline evoked response recorded by the
electrode prior to the triggering event.

19. The method of claim 17, further comprising provid-
ing, by the hearing device monitoring system based on the
determined operational effectiveness state, a notification to
the recipient regarding the triggering event.

20. The method of claim 17, wherein the operational
effectiveness state of the hearing device is indicative of
damage to at least one of the hearing device or the recipient
as a result of the triggering event.

\* \* \* \* \*